(12) United States Patent
Masilamani et al.

(10) Patent No.: US 11,098,089 B2
(45) Date of Patent: Aug. 24, 2021

(54) METHOD FOR HIGH LEVEL PRODUCTION OF $CRM_{197}$

(71) Applicant: Biological E Limited, Telangana (IN)

(72) Inventors: Balamurali Masilamani, Telangana (IN); Rajan Sriraman, Telangana (IN); Mandar Shirish Dixit, Telangana (IN); Deviprasanna Chakka, Telangana (IN); Satyam Naidu Sureddi, Telangana (IN); Ramesh Venkat Matur, Telangana (IN); Narender Dev Mantena, Telangana (IN); Mahima Datla, Telangana (IN)

(73) Assignee: BIOLOGICAL E LIMITED

( * ) Notice: Subject to any disclaimer, the term of this patent is extended or adjusted under 35 U.S.C. 154(b) by 0 days.

(21) Appl. No.: 16/606,958

(22) PCT Filed: Apr. 19, 2018

(86) PCT No.: PCT/IN2018/050235
§ 371 (c)(1),
(2) Date: Oct. 21, 2019

(87) PCT Pub. No.: WO2018/193475
PCT Pub. Date: Oct. 25, 2018

(65) Prior Publication Data
US 2020/0277341 A1     Sep. 3, 2020

(30) Foreign Application Priority Data

Apr. 22, 2017 (IN) .............................. 201741014335

(51) Int. Cl.
*C12N 1/20* (2006.01)
*A61K 39/05* (2006.01)
*A61K 39/385* (2006.01)
*C12P 21/00* (2006.01)
*C07K 14/34* (2006.01)

(52) U.S. Cl.
CPC .............. *C07K 14/34* (2013.01); *A61K 39/05* (2013.01); *A61K 39/385* (2013.01); *C12N 1/20* (2013.01); *C12P 21/00* (2013.01)

(58) Field of Classification Search
None
See application file for complete search history.

(56) References Cited

U.S. PATENT DOCUMENTS

| 6,962,803 | B2 | 11/2005 | Wolfe et al. |
| 2004/0087020 | A1 | 5/2004 | Olivieri et al. |
| 2011/0097359 | A1 | 4/2011 | Lee |

FOREIGN PATENT DOCUMENTS

| EP | 0616034 | 9/1994 |
| EP | 1849860 | 10/2007 |
| WO | WO 2006/100108 | 3/2006 |
| WO | WO 2011/123139 | 4/2010 |
| WO | WO 2013/068568 | 11/2012 |
| WO | WO 2015/134402 | 3/2015 |

OTHER PUBLICATIONS

Boyd et al., "Analysis of the Diphtheria tox Promoter by Site-Directed Mutagenesis," Journal of Bacteriology. 170(12):5949-5952 (publication date: Dec. 1988).
Currier "Isolation of covalently closed circular DNA of high molecular weight from bacteria," Anal Biochem. 76(2):431-41 (publication date: Dec. 1976).
Drew et al., "A chemically defined medium suitable for the production of high titer diphtherial toxin," J Bacteriol. 62(5):549-59 (1951).
Fass et al., "High-yield production of diphtheria toxin mutants by high-density culture of C7 (beta)tox+ strains grown in a non-deferrated medium," Appl Microbiol Biotechnol. 43(1):83-8 (publication date: Apr. 1995).
International Search Report and Written Opinion dated Oct. 25, 2018 for International Application No. PCT/IN2018/050235.
Nagarkar et al. "The amino acid requirements of Corynebacterium diphtheriae PW 8 substrain CN 2000," Journal of Applied Microbiology. 92(2):215-220 (publication date: Jan. 21, 2002).
Pushnova et al., "Quantitative restriction fragment length polymorphism: a procedure for quantitation of diphtheria toxin gene CRM197 allele," Anal Biochem. 260(1):24-9 (publication date: Jun. 1998).
Rappuoli et al.,"Isolation and characterization of Corynebacterium diphtheriae nontandem double lysogens hyperproducing CRM197," Applied and Environmental Microbiology. 560-564 (publication date: Sep. 1983).
Zhou et al., "Secretory expression of recombinant diphtheria toxin mutants in B. Subtilis," J of Tongji Univ. 19(4):253-256 (publication date: Jan. 1, 1999).

*Primary Examiner* — Oluwatosin A Ogunbiyi
(74) *Attorney, Agent, or Firm* — Perkins Coie LLP

(57) ABSTRACT

The present invention provides an improved method for the production of $CRM_{197}$ with high yield using engineered *Corynebacterium diphtheria* strain having an increased copy number of the $CRM_{197}$ gene, wherein the method comprises growing the strain in media free of animal-derived components with one or more amino acids.

18 Claims, 2 Drawing Sheets

METHOD FOR HIGH LEVEL PRODUCTION OF $CRM_{197}$

FIELD OF THE INVENTION

Figure 1:
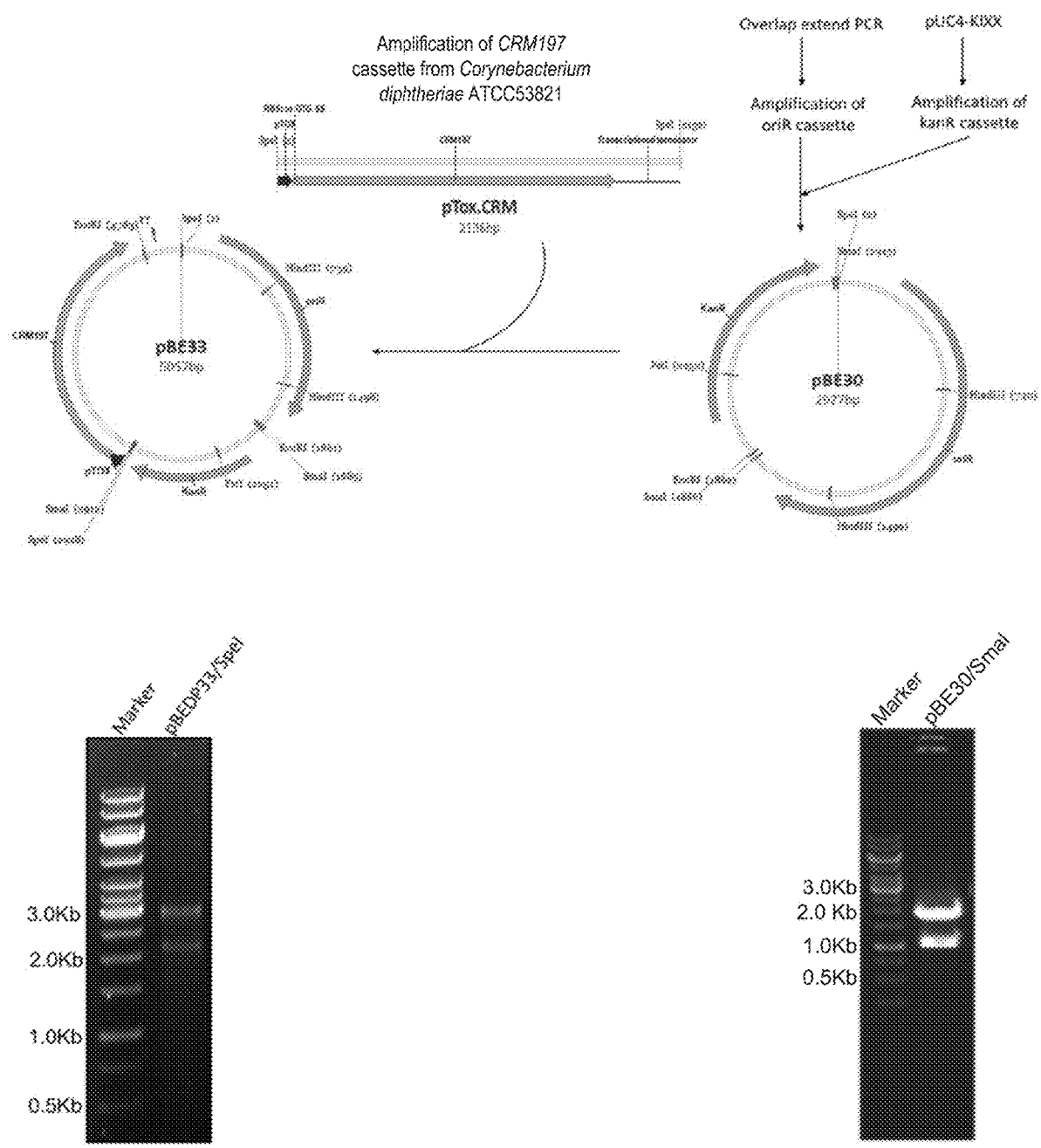

The present invention relates to an improved method for the production of $CRM_{197}$ with high yield using engineered *Corynebacterium diphtheriae* strain having increased copy number of $CRM_{197}$ gene.

BACKGROUND OF THE INVENTION $CRM_{197}$ is a genetically detoxified form of diphtheria toxin. A single mutation at position 52, substituting glutamic acid for glycine, causes the loss of ADP-ribosyltransferase activity of the native toxin. The structural basis of $CRM_{197}$ for the lack of toxicity has been elucidated and is widely used as a carrier protein for conjugate vaccines. $CRM_{197}$, like diphtheria toxin, is a single polypeptide chain of 535 amino acids (58.4 KD) consisting of two subunits (linked by disulfide bridges).

$CRM_{197}$ is used as a carrier protein in a number of approved conjugate vaccines such as *Haemophilus influenzae* type b conjugate marketed under the trade name Hibtiter TM, 13-valent pneumococcal polysaccharide conjugate marketed under the trade name PREVNAR 13® and the like.

Ruth M. Drew et al., Bacteriol. 1951 November; 62(5): 549-59; disclosed a chemically defined media suitable for the production of high titer diphtherial toxin and summarized the amino acid requirements of *Corynebacterium diphtheriae*, Toronto strain of Park-Williams no. 8. The media contains amino acids which effectively replace the animal derived component i.e. casein hydrolysate. The amino acids include glutamic acid, cystine, proline, tryptophan, leucine, valine, methionine, and glycine.

Rappuoli et al; *Applied and Environmental Microbiology* 1983 Vol. 46(3):560-564 have disclosed that the nontandem double lysogens were stable and capable of giving high yields of $CRM_{197}$, up to threefold higher than monolysogens.

R. Fass et al., *Applied Microbiology and Biotechnology*; April 1995, Volume 43(1): 83-88; disclosed a high-density growth approach to produce mutated diphtheria toxin from two strains of *Corynebacterium diphtheriae*: C7 (β) (tox-201, tox-9) and C7 (β)(tox-107). The procedure involves the use of a modified, non-deferrated growth media that provided fast and high-density growth of the bacteria, and which, when associated with simultaneous depletion of glucose and iron, enhanced the toxin production. Oxygen-enriched air was supplied to enable the bacteria to grow to a cell density giving an absorbance of 70 at 600 nm (15-20 g/L dry weight). The maximum toxin concentration in the culture supernatant was 150 mg/l.

Parag P. Nagarkar et al., *Journal of Applied Microbiology* 2002, 92, 215-220; disclosed the amino acid utilization pattern during growth of *Corynebacterium diphtheriae* and showed that only four of the nine amino acids tested, namely cystine, histidine, aspartate and methionine, were critical for growth and toxin production by *Corynebacterium diphtheriae*.

European Patent No. 1 849 860 B1 disclosed the use of proteinaceous material of non animal origin, such as proteins from soy beans, cotton seeds, potatoes, etc., as a media constituent for the cultivation of pathogenic bacteria.

U.S. Pat. No. 6,962,803 B2 disclosed a method of purifying diphtheria toxin by means of fermenting a microorganism strain capable of producing diphtheria toxin, said method comprising adding glucose to a growing culture whereby the addition of glucose maintains microorganism growth effective to support diphtheria toxin production. It further disclosed that in addition to a carbon source, there are other minimum nutritional requirements for growth which include trace metals, phosphate, a nitrogen source, generally casamino acids and yeast extract.

US Patent Application Publication No. 2011/0097359 A1 disclosed a media for culturing a strain of *Corynebacterium diphtheriae* to produce a level of diphtheria toxin or an analog thereof, wherein the media is substantiality free of animal derived products and comprises: water; a carbohydrate source; a nitrogen source; and a number of free amino acids in an initial concentration wherein the initial concentration of each free amino acid is not limiting for the level of production of the diphtheria toxin or the analog thereof. Further discloses that the carbohydrate source is free of glucose.

WO 2006/100108 A1 disclosed a fermentation process comprising a step of growing a strain of *Corynebacterium diphtheriae* in a media within the fermenter under conditions of agitation sufficient to maintain a homogenous culture and limited aeration such that $pO_2$ within the culture falls to less than 4% for the majority of the fermentation step. Further disclosed that the pH within the fermenter is held between 7.0 and 7.8 by the degree of aeration without requiring addition of acid or base.

The $CRM_{197}$ process is generally sensitive to small changes in process components as well as process parameters. The $CRM_{197}$ production from *Corynebacterium diphtheriae* is exercised across the globe albeit with limited success for commercial realization. None of the above references disclosed method of producing $CRM_{197}$ with high yields such as >150 mg/l using engineered *Corynebacterium diphtheriae* strain. The inventors of the present invention have developed a metabolic flux model for high yield production of $CRM_{197}$ using engineered *Corynebacterium diphtheriae* strain.

Objective of the Invention

It is the main objective of the present invention to provide an improved process for the high level production of $CRM_{197}$.

Yet another objective of the present invention is to provide an improved process for the high level production of $CRM_{197}$ which is cost effective and can be used for manufacturing conjugate vaccines.

Summary of the Invention

The present invention provides an improved method for the production of $CRM_{197}$ with high yield using engineered *Corynebacterium diphtheriae* strain having increased copy number of $CRM_{197}$ gene, wherein the method comprises growing the strain in a fermentation media comprising one or more amino acids and is free of animal derived components.

The present invention provides an improved method for the production of $CRM_{197}$ which method comprises culturing the engineered *Corynebacterium diphtheriae* strain having increased copy number of $CRM_{197}$ gene in a fermentation media which is free of animal derived components and comprises more than 10 amino acids and supplementing the media with nutrients.

The present invention also provides an improved method for the production of CRM$_{197}$ which method comprises culturing the engineered *Corynebacterium diphtheriae* strain having increased copy number of CRM$_{197}$ gene in a fermentation media which is free of animal derived components and comprises more than 10 amino acids and supplementing the media with nutrients based on metabolic flux model.

BRIEF DESCRIPTION OF THE DRAWINGS

FIG. 1—Construction of a plasmid designated as pBE33.

FIG. 2—The metabolic flux balance model flow chart.

DETAILED DESCRIPTION OF THE INVENTION

The present invention provides an improved method for the production of $CRM_{197}$ with high yield using engineered *Corynebacterium diphtheriae* strain having increased copy number of $CRM_{197}$ gene, wherein the method comprises growing the strain in a fermentation media comprising more than 10 amino acids and is free of animal derived components.

Engineered *Corynebacterium diphtheriae* strain (C7Ep) of the present invention refers to the *Corynebacterium diphtheriae* having episomally placed multiple copies of $CRM_{197}$ gene regulated by the same mechanism that of host $CRM_{197}$ gene and the said strain's genetic background is single lysogen.

The amino acids used in the present invention are selected from Alanine, Arginine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Valine and its salts and each amino acid is used in an amount of about 0.05 to 2 g/l.

The effect of amino acids, vitamins and the process conditions for the production of $CRM_{197}$ has been studied. It has been found that certain amino acids have shown negative effect on the growth of bacteria. However, it is found that the production of $CRM_{197}$ is increased if more than 10 amino acids are used in an optimum concentration. The concentration of amino acids is optimized using Plackett Burman design of experiments.

Plackett Burman designs are experimental designs for investigating the dependence of some measured quantity on a number of independent variables (factors), in such a way as to minimize the variance of the estimates of these dependencies using a limited number of experiments. The outcome showed amino acid such as Aspartic acid, Glutamine, Glycine isoleucine leucine, valine and at a temperature of 35 to 36° C. have positive impact on the $CRM_{197}$ synthesis and amino acids such as Alanine, Isoleucine, Valine and at temperature of 35 to 36° C. have negative effect in the synthesis of $CRM_{197}$. Several levels of Design of experiments were carried out at different concentrations to achieve high level production of $CRM_{197}$. The use of tyrosine and asparagine resulted in decrease in the overall yield of $CRM_{197}$ and hence these amino acids are not part of the invention.

In a preferred embodiment of the present invention, the fermentation media contains combination of Phenylalanine, Arginine and one or more other amino acids wherein the amount of Phenylalanine and Arginine used is about less than about 1 g/L.

In a more preferred embodiment of the present invention, the fermentation media comprise combination of Phenylalanine, Arginine and one or more other amino acids wherein amount of Phenylalanine is about 0.25 to 0.75 g/l and Arginine is about 0.1 to 0.5 g/l.

The present invention provides an improved method for the production of $CRM_{197}$ using engineered *Corynebacterium diphtheriae* strain having increased copy number of $CRM_{197}$ gene, wherein the method comprises growing the strain in a fermentation media comprising more than 10 amino acids, supplementing the media with vitamins in the range of about 0.05 to 20 mg per liter, wherein the media is free of animal derived components.

In another embodiment of the present invention, amino acids, vitamins, trace elements and the like are added as nutrients to the fermentation media during the cultivation.

Various nutrients used in the present invention as supplements include vitamins selected from Nicotinic acid, Thiamine, Pantothenic acid, Biotin, Riboflavin, FolicAcid; Pimelic acid; phosphate, a nitrogen source and trace metals and the like and each vitamin is used in an amount in the range from about 0.05 to 20 mg per liter.

The fermentation media used in the present invention is a non-defferated and completely free from animal derived components. Further, the media is also devoid of traditional meat based Loeffler media and casamino acid based defferated low iron YC media. The components of fermentation media of the present invention comprises Yeast Extract, Veg.Peptone, Potassium-dihydrogen phosphate ($KH_2PO_4$), Tryptophan, Glucose, YC Trace salt solution.

In another embodiment of the present invention, the media composition for the cultivation of engineered *Corynebacterium diphtheriae* strain having increased copy number of $CRM_{197}$ gene comprises base fermentation media comprising Yeast Extract, Veg.Peptone, Potassium-dihydrogen phosphate ($KH_2PO_4$), Tryptophan, Glucose, YC Trace salt solution; one or more amino acids, vitamins, trace elements and the like.

Suitable trace metals include Potassium, Magnesium, Calcium, Chloride, Choline, Copper, Manganese, Sulfate, Zinc and the like.

The present invention provides an improved method for the production of $CRM_{197}$ using engineered *Corynebacterium diphtheriae* strain having increased copy number of $CRM_{197}$ gene, wherein the method comprises supplementing the fermentation media with nutrients based on metabolic flux model.

Metabolic flux model refers to the complete network of Heat Transfer, Mass Transfer, Oxygen transfer rate (OTR), Oxygen uptake rate (OUR) and Ion transfer kinetics wherein OTR is being maintained by means of agitation, back pressure and pump in pure oxygen. This model is depicted in FIG. 2.

Development of Metabolic Flux Model.

This model is created on the basis of online data interpretation of hydrogen ions accumulations in the process as a primary variable which is followed by the dissolved oxygen, oxygen to $CO_2$ conversion along with the heat liberated in the process. For example the model works on the carbon source limitation conditions. The carbon source is pulsed and the response is evaluated in the process. The corrective action was taken on hydrogen ions generation based on the response. Then the feed was optimized to get a steady pH and dissolved oxygen (DO) and heat transfer rate (For eg pH of 7.4; residual DO of >2 to 20; Heat transfer rate HTR).

In an embodiment of the present invention, the method comprises supplementing the media with glucose during the entire fermentation process.

The present invention does not involve the use of maltose as a carbon source and deferration step.

$CRM_{197}$ produced according to the present invention can be used for manufacturing conjugate vaccines such as pneumococcal conjugate, typhoid conjugate, Hib conjugate and the like.

In yet another embodiment, the present invention provides an improved method for the production of $CRM_{197}$ which method comprises culturing the engineered *Corynebacterium diphtheriae* strain having increased copy number of $CRM_{197}$ gene in a fermentation media which is free of animal derived components and comprises more than 10 amino acids and supplementing the media with nutrients based on metabolic flux model, wherein the amino acids are selected from Alanine, Arginine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Valine and its salts.

In yet another embodiment, the present invention provides an improved method for the production of $CRM_{197}$ which method comprises culturing the engineered *Corynebacterium diphtheriae* strain having increased copy number of $CRM_{197}$ gene in a fermentation media which is free of animal derived components and comprises more than 10 amino acids, wherein each amino acid is used in an amount of about 0.05 to 2 g/l.

In yet another embodiment, the present invention provides an improved method for the production of $CRM_{197}$ which method comprises culturing the engineered *Corynebacterium diphtheriae* strain having increased copy number of $CRM_{197}$ gene in a fermentation media which is free of animal derived components and comprises more than 10 amino acids and supplementing the media with nutrients based on metabolic flux model, wherein each amino acid is used in an amount of about 0.05 to 2 g/l.

In yet another embodiment, the present invention provides an improved method for the production of $CRM_{197}$ which method comprises culturing the engineered *Corynebacterium diphtheriae* strain having increased copy number of $CRM_{197}$ gene in a fermentation media which is free of animal derived components and comprises base media, more than 10 amino acids and supplementing the media with nutrients based on metabolic flux model, wherein each amino acid is used in an amount of about 0.05 to 2 g/l.

In yet another embodiment, the present invention provides an improved method for the production of $CRM_{197}$ which method comprises culturing the engineered *Corynebacterium diphtheriae* strain having increased copy number of $CRM_{197}$ gene in a fermentation media which is free of animal derived components and comprises more than 10 amino acids and supplementing the media with nutrients based on metabolic flux model, wherein the amino acids are selected from Alanine, Arginine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Valine and its salts wherein each amino acid is used in an amount of about 0.05 to 2 g/l.

In yet another embodiment, the present invention provides an improved method for the production of $CRM_{197}$ which method comprises culturing the engineered *Corynebacterium diphtheriae* strain having increased copy number of $CRM_{197}$ gene in a fermentation media which is free of animal derived components and comprises more than 10 amino acids, wherein the amino acids are selected from Alanine, Arginine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Valine and its salts wherein each amino acid is used in an amount of about 0.05 to 2 g/l.

In a preferred embodiment, the present invention provides an improved method for the production of $CRM_{197}$ which method comprises
  i) culturing the engineered *Corynebacterium diphtheriae* strain having increased copy number of $CRM_{197}$ gene in a fermentation media which is free of animal derived components and comprises base media and more than 10 amino acids selected from Alanine, Arginine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Valine and its salts and
  ii) supplementing the media with glucose and nutrients based on metabolic flux model.

In yet another embodiment, during the fermentation process temperature is maintained in the range from 30 to 40° C. and pH is maintained at 7.0 to 8.0, preferably 7.4 to 7.6 using 20% orthophosphoric acid, 12.5% ammonium hydroxide. The fermentation process is carried out for a period of 15 to 24 hours, preferably 16 to 20 hours.

In an embodiment, the present invention provides fermentation composition and process which is devoid of tyrosine and asparagine. In an embodiment, the process of the present invention is devoid of casamino acid based defferated low iron YC media, maltose as a carbon source and deferration step.

The present invention provides an improved method for the production of $CRM_{197}$ which method comprises culturing the engineered *Corynebacterium diphtheriae* strain having increased copy number of $CRM_{197}$ gene in a fermentation media which is free of animal derived components and contains combination of Phenylalanine, Arginine in an amount of about less than 1 g/L and one or more other amino acids.

In an embodiment, the present invention provides an improved method for the production of $CRM_{197}$ which method comprises culturing the engineered *Corynebacterium diphtheriae* strain having increased copy number of $CRM_{197}$ gene in a fermentation media which is free of animal derived components and comprises more than 10 amino acids and supplementing the media with nutrients based on metabolic flux model, wherein the yield of $CRM_{197}$ obtained is more than 150 mg/L.

In an embodiment, the present invention enables making a conjugate vaccine which comprises conjugating polysaccharides from *Salmonella typhi, Streptococcus pneumoniae*, meningococcus, *Haemophilus influenzae* with $CRM_{197}$ prepared according to the present invention.

The present invention provides an improved method for the production of $CRM_{197}$ with high yield using engineered *Corynebacterium diphtheriae* strain having increased copy number of $CRM_{197}$ gene, wherein the method comprises growing the strain in media free of animal derived components comprising more than 10 amino acids and supplementing the media with nutrients based on metabolic flux model.

In an embodiment, the present invention provides an improved method for the production of $CRM_{197}$ with yields such as 150 mg/L, 200 mg/L, 300 mg/L, 500 mg/L, 1 g/L, 1.5 g/L, 2 g/L, 2.5 g/L, 3 g/L, 3.5 g/L, 4 g/l, 4.5 g/L, and 5 g/L.

In an embodiment, the present invention provides an engineered *Corynebacterium diphtheriae* strain C7 (β 197) wherein pBE33 plasmid was transferred by electroporation.

The CRM$_{197}$ produced according to the present invention has been quantified with Immuno-Capture Enzyme Linked Immuno-Sorbent Assay (IC-ELISA).

Development of Engineered *Corynebacterium diphtheriae* Strain Having Increased Copy Number of CRM$_{197}$ Gene on an Expression Vector Plasmid.

*Corynebacterium diphtheriae* C7 (β-197) ATCC 53821, the gene encoding for $CRM_{197}$ exists as single copy and mutant $CRM_{197}$ protein is secreted into the culture media under iron regulation. The yield of $CRM_{197}$ increases three-fold in *Corynebacterium diphtheriae* C7 strain that have two copies of the corynephage-beta (ATCC 39255). This suggests that gene copy number is linked to increased productivity. In order to make $CRM_{197}$ production from *Corynebacterium diphtheriae* commercially viable it is desired to increase the expression level. Integrating more copy number into bacterial genome is technically challenging. The multi copy phage integrants are genetically unstable and lose the additional copies of the CRM gene. The present inventors intended to improve the expression levels of the $CRM_{197}$ by increasing the gene copies of $CRM_{197}$ delivered on plasmids having an antibiotic selection marker, along with the native regulatory elements of $CRM_{197}$. Accordingly, the inventors have developed *Corynebacterium diphtheriae* strain having increased copy number of $CRM_{197}$ gene, evaluated the strain's stability. The modified strain had higher levels of $CRM_{197}$ expression compared to un modified *Corynebacterium* strains.

The present invention is more specifically illustrated with reference to the examples given below. However, it should be understood that the present invention is not limited by an example in any manner but includes variations thereof within the parameters described herein, as can be known to those well-versed in the art.

Example 1

Improvement of $CRM_{197}$ Expression by Episomal Copy of $CRM_{197}$:

A vector that can stably replicate in *Corynebacterium diphtheriae* C7 (β 197) was prepared. Isolation of Native plasmid from *Corynebacterium* C7 *diphtheriae* has been carried out using large plasmid isolation protocol as described in Thomas C. Currier et al., Anal Biochem. 1976; 76(2): 431441. Using the native plasmid DNA preparation, 1.87 Kb origin of replication (oriR) was amplified. Simultaneously, 1.033 Kb kanR sequence was amplified using pUC4-KIXX template DNA and blunt end ligated to oriR to generate pBE30. Further a 2.13 Kb gene sequence of $CRM_{197}$ comprising pTox promoter region (Boyd et al., 1988), cru and predicted terminator sequence was amplified from *Corynebacterium diphtheriae* C7 (β 197) genomic DNA and cloned into the unique SpeI restriction site designed in the pBE30. The GAG mutation in this amplicon was verified by allele specific PCR assay (Pushnova et al., *Analytical Biochemistry.* 1998; 260: 24 to 29) and DNA sequencing. The plasmid thus obtained was designated as pBE33 (FIG. 1).

The pBE33 plasmid was transferred by electroporation following the procedures optimized for *Corynebacterium diphtheriae* C7 (β 197). The transformed *Corynebacterium diphtheriae* C7 (β 197) (pBE33) colonies were confirmed by specific colony PCR and plasmid isolation and restriction digestion. Expression of $CRM_{197}$ in colonies was analyzed by SDS-PAGE and Western blotting. The $CRM_{197}$ in the media was quantified by ELISA and HPLC and were presented as concentration of $CRM_{197}$ expressed per liter of the culture media.

Example 2

Production of $CRM_{197}$ with Engineered *Corynebacterium diphtheriae* C7Ep Strain on Base Media—Free of Animal Derived Components.

*Corynebacterium diphtheriae* C7Ep strain was used for this process. A two-step cultivation was followed for inoculum preparation in shake flask. Media for shake flask cultivation comprises of Yeast Extract (YE) 10 g/L, Veg. Peptone 15 g/L, $KH_2PO_4$ 4.3 g/L, Tryptophan 50 mg/L, Glucose 4.0 g/L, Nicotinic acid 0.8 mg/L, Pimelic acid 0.08 mg/L, $CuSO_4$. $5H_2O$ 25 mg/L, $ZnSO_4$. $5H_2O$ 12.5 mg/L, $MnCl_2$. $4H_2O$ 6.25 mg/L, Cystine 0.5 g/L, Kanamycin 25 mg/L, Glucose 4.0 g/L.

To a 20 L fermenter media, 5% inoculum was added to start the process. Media for fermenter cultivation comprises of YE 15 g/L, Veg.Peptone 30 g/L, $KH_2PO_4$ 4.3 g/L, Tryptophan 50 mg/L, Nicotinic acid 0.8 mg/L, Pimelic acid 0.08 mg/L, $CuSO_4$. $5H_2O$ 25 mg/L, $ZnSO_4$. $5H_2O$ 12.5 mg/L, $MnCl_2$. $4H_2O$ 6.25 mg/L, Cystine 0.5 g/L, Kanamycin 25 mg/L, Glucose 4.0 g/L.

The culture was stirred at 300 RPM throughout the batch. Temperature was maintained at 35° C. and pH was maintained at 7.4 using 20% orthophosphoric acid and 5 N NaOH. The culture was aerated using 1.0 vvm air. Culture was enriched with oxygen to maintain Dissolved Oxygen (DO) level to 20%. After first few hours, DO levels keeps falling below 20% when limit of 02 enrichment is reached. The DO level for rest of the batch remains close to zero with rise towards end hours. When residual glucose in the broth falls below 0.5 g/L, 40% glucose feed was given with 2 g/L/hr. Batch was harvested after 14 hrs of cultivation when cell densities reached about 90 units of OD 600 nm. The foam in the reactor was controlled by 30% organic antifoam. The $CRM_{197}$ production was reached to a titer of 60 to 65 mg/L of fermentation broth.

A fermentation run under similar conditions using unengineered *Corynebacterium diphtheriae* C7 $CRM_{197}$ strain produced about 35 to 40 mg/L of $CRM_{197}$ which is less than engineered strain. This shows the influence of the extra gene copies towards increased production of the $CRM_{197}$.

Example 3

Production of $CRM_{197}$ with Engineered *Corynebacterium diphtheriae* C7Ep Strain on Base Media Free of Animal Derived Components by Following the Metabolic Flux Balance Model.

*Corynebacterium diphtheriae* C7Ep strain was used for this process. A two-step cultivation was followed for inoculum preparation in shake flask. Media for shake flask cultivation comprises of YE 10 g/L, Veg. Peptone 15 g/L, $KH_2PO_4$ 4.3 g/L, Tryptophan 50 mg/L, Glucose 4.0 g/L Nicotinic acid 0.8 mg/L, Pimelic acid 0.08 mg/L, $CuSO_4$. $5H_2O$ 25 mg/L, $ZnSO_4$. $5H_2O$ 12.5 mg/L, $MnCl_2$. $4H_2O$ 6.25 mg/L, Cystine 0.5 g/L, Kanamycin 25 mg/L, Glucose 4.0 g/L.

To a 20 L fermenter media, 5% inoculum was added to start the process. Media for fermenter cultivation comprises of YE 15 g/L, Veg. Peptone 30 g/L, $KH_2PO_4$ 4.3 g/L, Tryptophan 50 mg/L, Nicotinic acid 0.8 mg/L, Pimelic acid 0.08 mg/L, $CuSO_4$. $5H_2O$ 25 mg/L, $ZnSO_4$. $5H_2O$ 12.5 mg/L, MnCl$_2$. 4H$_2$O 6.25 mg/L, Cystine 0.5 g/L, Kanamycin 25 mg/L, Glucose 4.0 g/L.

The culture was stirred at 300 RPM throughout the batch. Temperature was maintained at 35° C. and pH was maintained at 7.4 using 20% orthophosphoric acid and 12.5% ammonium hydroxide. The culture was aerated using 1.0 vvm air. Culture was enriched with oxygen to maintain DO level to 20%. A model was introduced which follows the metabolic rate of conversion in the given point of time, this model takes the input from the online parameter of residual DO in correspondence with the changes with respect to pH, CO$_2$, heat generation. In log phase, DO levels keeps falling below 20% despite O$_2$ enrichment limit has reached. The DO level for rest of the batch remains close to zero with rise towards end hours. When residual glucose in the broth fall below 0.5 g/L, 40% glucose feed was fed in order to justify the metabolic flux model. Batch was harvested after 14 hrs of cultivation when cell densities reached about 90 units of OD 600 nm. The foam in the reactor was controlled by 30% organic antifoam. The CRM$_{197}$ production was reached to a titer of 150 mg/L of fermentation broth.

Example 4

Production of CRM$_{197}$ According to the Present Invention

A three-step cultivation was followed for inoculum preparation. First two steps were done in the shake flasks. Media for shake flask cultivation comprises of YE 10 g/L, Veg.Peptone 15 g/L, KH$_2$PO$_4$ 4.3 g/L, Tryptophan 50 mg/L, Glucose 4.0 g/L, YC Trace salt solution 2 ml/L, Cystine supplement 1 ml/L, Kanamycin 25 mg/L, Glucose 4.0 g/L.

The base media composition for seed fermentor was YE 15 g/L, Veg.Peptone 30 g/L, KH$_2$PO$_4$ 4.3 g/L, Tryptophan 50 mg/L, Nicotinic acid 0.8 mg/L, Pimelic acid 0.08 mg/L, CuSO$_4$. 5H$_2$O 25 mg/L, ZnSO$_4$. 5H$_2$O 12.5 mg/L, MnCl$_2$. 4H$_2$O 6.25 mg/L, Cystine 0.5 g/L, Kanamycin 25 mg/L, Glucose 4.0 g/L Given below is the fermenter media composition (Table I) and the ingredients which has been designed following the Placket Burmann design.

TABLE I

| S. No | Media components | Quantity | Units |
|---|---|---|---|
| 1 | Alanine | 0.1 | g/L |
| 2 | Arginine | 0.1 | g/L |
| 3 | Aspartic acid | 0.5 | g/L |
| 4 | Cysteine | 0.5 | g/L |
| 5 | Glutamic acid | 1 | g/L |
| 6 | Glutamine | 0.1 | g/L |
| 7 | Glycine | 0.5 | g/L |
| 8 | Histidine | 1 | g/L |
| 9 | Isoleucine | 1 | g/L |
| 10 | Leucine | 0.5 | g/L |
| 11 | Lysine | 0.1 | g/L |
| 12 | Methionine | 1 | g/L |
| 13 | Phenyl alanine | 0.5 | g/L |
| 14 | Proline | 0.1 | g/L |
| 15 | Serine | 0.1 | g/L |
| 16 | Threonine | 0.1 | g/L |
| 17 | Tryptophan | 0.1 | g/L |
| 18 | Valine | 1 | g/L |
| 19 | Potassium | 2 | g/L |
| 20 | Magnesium | 1 | g/L |
| 21 | Thiamine | 0.1 | mg/L |
| 22 | Biotin | 4 | mg/L |
| 23 | Calcium | 2 | mg/L |
| 24 | Chloride | 0.5 | mg/L |
| 25 | Choline | 0.1 | mg/L |
| 26 | Copper | 10 | mg/L |
| 27 | Folic Acid | 1.6 | mg/L |
| 28 | Manganese | 1 | mg/L |
| 29 | Nicotinamic Acid | 100 | mg/L |
| 30 | Pantothenic Acid | 50 | mg/L |
| 31 | Pimelic acid | 20 | mg/L |
| 32 | Riboflavin | 50 | mg/L |
| 33 | Sulfate | 20 | mg/L |
| 34 | Zinc | 7 | mg/L |

Figure 2:
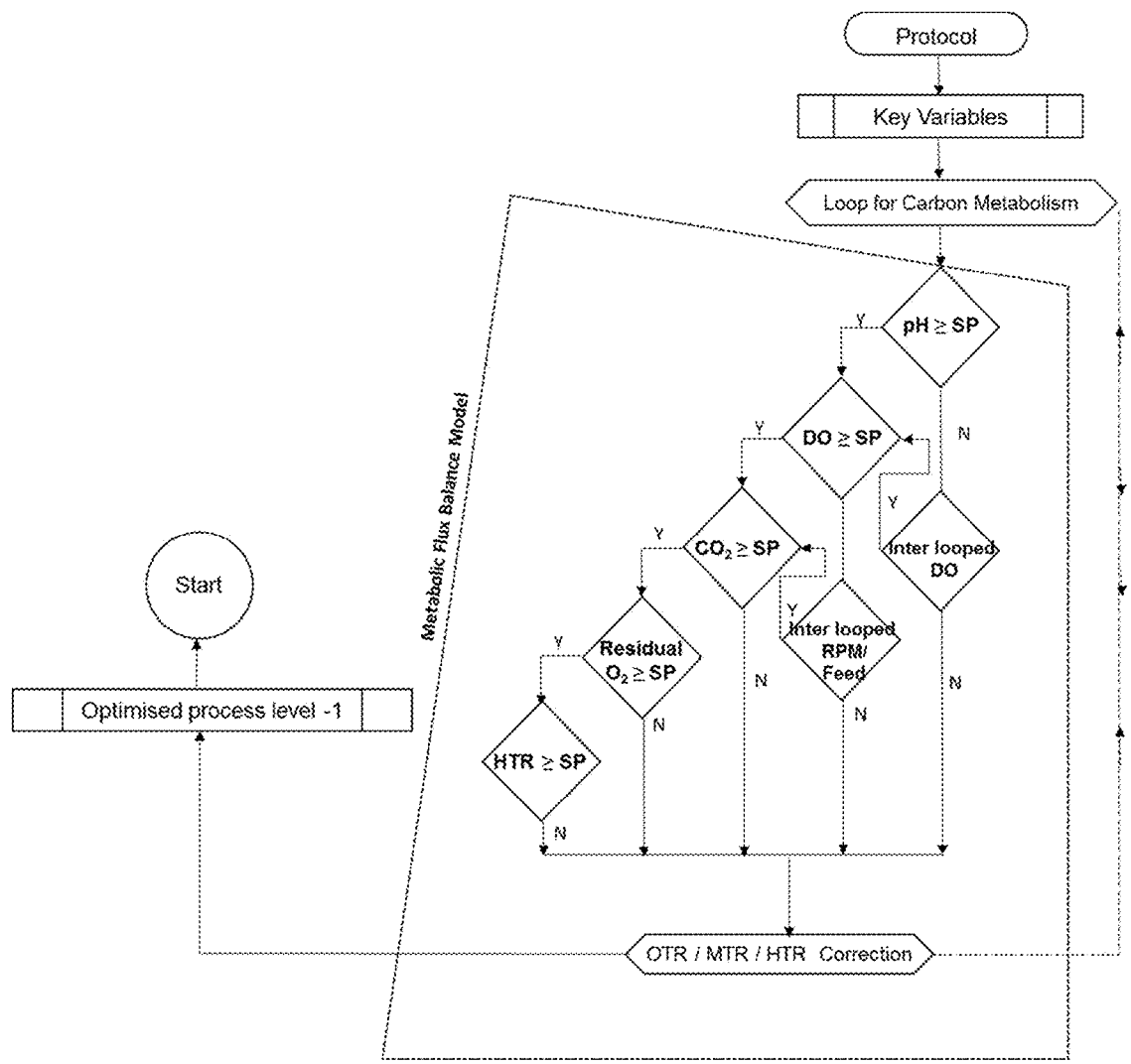

To a 20 L fermenter with above components with the base media (YE 15 g/L, Veg.Peptone 30 g/L, KH$_2$PO$_4$ 4.3 g/L, Tryptophan 50 mg/L, Nicotinic acid 0.8 mg/L, Pimelic acid 0.08 mg/L, CuSO$_4$. 5H$_2$O 25 mg/L, ZnSO$_4$. 5H$_2$O 12.5 mg/L, MnCl$_2$. 4H$_2$O 6.25 mg/L, Cystine 0.5 g/L, Kanamycin 25 mg/L, Glucose 4.0 g/L.), 5% inoculum from seed fermenter was added to start the process. Temperature was maintained at 35° C. and pH was maintained at 7.4 to 7.6 using 20% orthophosphoric acid, 12.5% ammonium hydroxide, and model based on metabolic flux (FIG. 2) modulation of glucose feeding and OTR. The culture was aerated using 1.0 vvm air. Culture was enriched with oxygen to maintain DO level to 20%. In log phase, DO levels keeps falling below 20% despite O$_2$ enrichment limit has reached. The DO level for rest of the batch remains close to zero with rise towards end hours. When residual glucose in the broth falls below 0.5 g/L, feed with 40% glucose solution was given at 4.5 g/L/hr. Intermittently vitamins and trace elements were supplemented at following levels; Nicotinic acid 6.425 mg/L, Pimelic acid 0.465 mg/L, CuSO$_4$. 5H$_2$O 25 mg/L, ZnSO$_4$. 5H$_2$O 12.5 mg/L, MnCl$_2$. 4H$_2$O 6.25 mg/L, Thiamine 0.08 mg/L, Pantothenic acid 0.25 mg/L, Biotin 0.006 mg/L, Riboflavin 0.3 mg/L, Folic Acid 0.06 mg/L. The batch was harvested after 18 hrs of cultivation when cell densities reached about 132 units of OD 600 nm. The foam in the reactor was controlled by 30% organic antifoam. The CRM$_{197}$ production reached a titer of 450 to 500 mg/L of fermentation broth.

Example 5

Comparison of CRM$_{197}$ Yields Using Native *Corynebacterium diphtheriae* C7 and an Engineered Strain of *Corynebacterium diphtheriae* C7Ep.

A fermentation was carried out using basic animal free media, Pre model Process Improvements and Media and process as per the Present invention using Native C7 *Corynebacterium diphtheriae* and engineered *Corynebacterium diphtheriae* strain.

The single lysogenic *Corynebacterium diphtheriae* strain C7 and engineered strain with episomally placed extra copies of $CRM_{197}$ gene (C7Ep) were used for process optimization. In a typical non deferrated YC media having animal components, C7 gave 22 to 25 mg/L of $CRM_{197}$ whereas C7Ep gave 40 to 45 mg/L. When media was modified by replacing the animal components by veg peptones, the C7 strain resulted in 40 to 45 mg/L of $CRM_{197}$ and C7Ep gave 65 mg/L of $CRM_{197}$. Process conditions when modified by changing the parameters, C7Ep produced 120 to 150 mg/L of $CRM_{197}$. A model was developed using inputs from the base process. The final outcome of the optimized method which resulted in 120 mg/l of $CRM_{197}$ from C7 and >500 mg/L of $CRM_{197}$ from C7Ep. The yields are compared in Table II given below:

TABLE II

Yield comparison of Native C7 - *Corynebacterium diphtheriae* with that of episomally modified C7Ep at different process condition.

| S. No | Organism | Yields of $CRM_{197}$ in mg/L by ELISA | | |
|---|---|---|---|---|
| | | Basic Animal free media | Pre model Process Improvements | Media and process as per the Present invention |
| 1 | *Corynebacterium* C7 (Native) | 20-25 | 35-40 | 110-120 |
| 2 | *Corynebacterium* C7 Ep ( Episome incorporated extra copy of gene) | 60-65 | 120-150 | >500 |

The invention claimed is:

1. A method for producing $CRM_{197}$, the method comprising growing a strain of *Corynebacterium diphtheriae* in a non-deferrated fermentation media free of animal derived components and comprising 10 or more amino acids, wherein the amino acids are not tyrosine or asparagine, and wherein the non-deferrated fermentation media is free of maltose.

2. The method of claim 1, comprising supplementing the fermentation media with nutrients.

3. The method of claim 2, wherein supplementing the fermentation media with nutrients comprises using metabolic flux.

4. The method of claim 1, wherein the 10 or amino acids are selected from the group consisting of alanine, arginine, aspartic acid, cysteine, glutamic acid, glutamine, glycine, histidine, isoleucine, leucine, lysine, methionine, phenylalanine, proline, serine, threonine, tryptophan, valine and salts thereof.

5. The method of claim 4, wherein the 10 or more amino acids are present in the non-deferrated fermentation media in an amount of about 0.05 g/L to about 2 g/L.

6. The method of claim 1, wherein the non-deferrated fermentation media comprises phenylalanine and arginine in an amount less than about 1 g/L.

7. The method of claim 2, wherein the nutrients are selected from the group consisting of nicotinic acid, thiamine, pantothenic acid, biotin, riboflavin, folic acid, pimelic acid phosphate, a nitrogen source and trace metals.

8. The method of claim 1, wherein the non-deferrated fermentation media composition comprises a base fermentation media, wherein the base fermentation media comprises yeast extract, vegetable peptone, potassium-dihydrogen phosphate ($KH_2PO_4$), tryptophan, and glucose.

9. The method of claim 1, further comprising supplementing the non-deferrated fermentation media with glucose.

10. A method of producing $CRM_{197}$, the method comprising:

(i) culturing a *Corynebacterium diphtheriae* strain having an increased copy number of $CRM_{197}$ gene in a non-deferrated fermentation media comprising a base media and 10 or more amino acids selected from the group consisting of alanine, arginine, aspartic acid, cysteine, glutamic acid, glutamine, glycine, histidine, isoleucine, leucine, lysine, methionine, phenylalanine, proline, serine, threonine, tryptophan, valine and salts thereof, and (ii) supplementing the non-deferrated fermentation media with glucose and nutrients using metabolic flux, wherein the non-deferrated fermentation media is free of maltose.

11. A method of producing $CRM_{197}$, the method comprising culturing a *Corynebacterium diphtheriae* strain having an increased copy number of $CRM_{197}$ gene in a non-deferrated fermentation media free of animal derived components and comprising 10 or more amino acids, and supplementing the non-deferrated fermentation media with nutrients using metabolic flux, wherein each of the 10 or more amino acids is present in the non-deferrated fermentation media in an amount of about 0.05 g/L to 2 g/L, wherein the amino acids are not tyrosine or asparagine, and wherein the non-deferrated fermentation media is free of maltose.

12. The method of claim 10, wherein the method is carried out at a temperature between 30 to 40° C. and at a pH of 7.0 to 8.0.

13. The method of claim 10, wherein the method yields 50 mg/L to 500 mg/L of $CRM_{197}$.

14. A method for manufacturing conjugate vaccine which comprises conjugating polysaccharides from *Salmonella typhi, Streptococcus pneumoniae, Haemophilus influenzae* with $CRM_{197}$ prepared according to claim 1.

15. The method of claim 11, wherein the method is carried out at a temperature between 30 to 40° C. and at a pH of 7.0 to 8.0.

16. The method of claim 11, wherein the method yields 50 mg/L to 500 mg/L of $CRM_{197}$.

17. A method for manufacturing conjugate vaccine which comprises conjugating polysaccharides from *Salmonella typhi, Streptococcus pneumoniae, Haemophilus influenzae* with $CRM_{197}$ prepared according to claim 10.

18. A method for manufacturing conjugate vaccine which comprises conjugating polysaccharides from *Salmonella typhi, Streptococcus pneumoniae, Haemophilus influenzae* with $CRM_{197}$ prepared according to claim 11.

* * * * *